United States Patent [19]

Ingram

[11] Patent Number: 5,549,622

[45] Date of Patent: Aug. 27, 1996

[54] METHOD FOR ALTERING THE CURVATURE OF THE CORNEA

[76] Inventor: Ronald W. Ingram, 3101 Stanolind Ave., Midland, Tex. 79705

[21] Appl. No.: 402,105

[22] Filed: Mar. 10, 1995

[51] Int. Cl.⁶ ............................................ A61F 9/00
[52] U.S. Cl. ............................ 606/166; 606/167
[58] Field of Search .................. 606/166, 167

[56] References Cited

U.S. PATENT DOCUMENTS

| | | | |
|---|---|---|---|
| 4,127,109 | 11/1978 | Fourney et al. | 128/1 R |
| 4,781,187 | 11/1988 | Herrick | 128/305 |
| 4,880,017 | 11/1989 | Soll et al. | 128/898 |
| 5,090,425 | 2/1992 | Stahl | 128/898 |
| 5,376,099 | 12/1994 | Ellis et al. | 606/166 |

*Primary Examiner*—Michael Powell Buiz
*Assistant Examiner*—Mark Leonardo
*Attorney, Agent, or Firm*—Peter J. Thoma

[57] ABSTRACT

A method for altering the curvature of the cornea of an eye includes the steps of making pairs of closely spaced, parallel incisions at predetermined sites on the surface of the cornea; removing the corneal tissue disposed between the incisions in each pair of incisions; and closing the incision at each site to exert a force on the cornea which increases its curvature. An instrument for altering the curvature of the cornea includes a shaft, a cutting tool mounted at one end of the shaft, the cutting tool having two parallel blades separated by a predetermined distance for making pairs of closely spaced, parallel incisions in a patient's cornea. The method and instrument enable correction for hyperopia and other types of refractive errors of the eye.

17 Claims, 2 Drawing Sheets

5,549,622

METHOD FOR ALTERING THE CURVATURE OF THE CORNEA

TECHNICAL FIELD OF THE INVENTION

This invention relates generally to the field of eye surgery, and more particularly, to a method and instrument for altering the curvature of the cornea.

BACKGROUND OF THE INVENTION

Myopia and hyperopia are refractive errors that may occur in one or both eyes. Myopia or nearsightedness occurs when light rays entering the eye focus in front of the retina rather than directly on it, as in the normal eye. Myopia often results when the curvature of the cornea is too steep. In contrast, hyperopia or farsightedness occurs when light rays entering the eye focus behind, instead of directly on, the retina. With hyperopia, the curvature of the cornea is too flat. Ordinarily, the error in the focal point of light entering the eye is corrected with glasses or contact lenses so that a clear, sharp image is formed on the retina and transmitted to the brain.

Over the years, eye surgeons have developed various surgical procedures to correct these refractive errors. One of the most common techniques is radial keratotomy (RK), a surgical procedure used to correct myopia; it is not used to correct hyperopia. During RK, a surgeon makes a series of single-cut incisions in the surface of the cornea in order to flatten it. The change in the curvature of the cornea moves the point at which light focuses from a position forward of the retina to a position directly on the retina.

Automated lamellar keratoplasty (ALK) is another technique utilized to correct refractive errors in the eye. An essential step in this procedure is slicing a portion off of the top layer of the cornea. This technique is used to correct hyperopia, higher degrees of myopia and presbyopia, a condition where the lens inside the eye loses its ability to focus on near objects.

During ALK, an automated device containing an oscillating blade cuts across the central cornea over the pupil, leaving the deeper layers of the cornea uncut. A thin disc of corneal tissue is removed. Intraocular pressure inside the eye pushes the uncut corneal layers outward, increasing the curvature of the cornea. Then the removed disc of corneal tissue is replaced. These steps correct the hyperopic eye. In the myopic eye, two discs of tissue may be removed from the cornea and the first disc replaced, to decrease the original curvature of the cornea.

A third corrective procedure known in the art is hexagonal keratotomy (HK). This technique involves making a hexagonally-shaped incision surrounding the pupil, effectively creating an "island" around the pupil. Pressure inside the eye forces the "island" outward, increasing the curvature of the cornea. This procedure is used to decrease hyperopia and to increase myopia.

A fourth corrective procedure known in the art is Photorefractive Keratectomy Laser surgery (PKL). With this method, a laser vaporizes portions of the cornea to flatten it in order to correct myopia. The PKL technique is also used to correct hyperopia by burning off more peripheral cornea tissue in order to recontour the corneal surface.

Another corrective procedure known in the art is Astigmatic Keratotomy (AK). This procedure is essentially a subtype of RK wherein transverse and radial incisions are made in the cornea.

Another corrective procedure known in the art involves using implants to surgically correct refractive errors. For example, U.S. Pat. No. 4,781,187 to Herrick teaches a method and implant to correct hyperopia by inserting a triangular implant into an incision made in the cornea. One may correct other refractive errors such as myopia using this method by inserting an implant having a different shape.

Although the above-described techniques have been widely used in conjunction with the correction of refractive errors, they are not entirely satisfactory. For example, although it usually corrects myopia, RK sometimes produces certain undesirable side effects, including overcorrection. In other words, the adjustment made by the RK procedure causes the cornea to flatten too much, with the result that the focal point of the eye lies behind the retina, producing hyperopia. This is effectively the condition that naturally exists with farsighted individuals.

The ALK procedure is very unpredictable in its results and may also result in overcorrection. ALK is a more complicated surgical procedure than RK and has the inherent disadvantage of cutting the cornea directly over the pupil, through which the light of vision passes. In contrast, RK employs radial incisions which do not extend across the pupil. In addition, the ALK and HK procedures are not feasible methods to repair overcorrection in eyes that have previously undergone an RK procedure.

Single-blade instruments for use in RK procedures are well known in the art. For example, U.S. Pat. No. 5,376,099 to KMI, Inc. teaches an instrument wherein the blade includes a projecting, short cutting edge and a recessed blunt edge. This instrument is not designed to handle the reversal of overcorrected RKs or naturally occurring hyperopia.

Thus, there is a need for a method and instrument for reversing an overcorrected RK surgery and for correcting a naturally occurring hyperopic eye that does not include the above-described disadvantages.

SUMMARY OF THE INVENTION

The present invention comprises a method and instrument for altering the curvature of the cornea that overcomes the disadvantages associated with the prior art. A method for altering the curvature of the cornea comprises the steps of making pairs of closely spaced, symmetrical, radial incisions in the cornea; removing the corneal tissue between the pairs of incisions; and closing the incisions to exert a force on the cornea which increases its curvature.

An instrument for altering the curvature of the cornea comprises a shaft, a cutting tool mounted at one end of the shaft and having at least two parallel cutting blades separated by a predetermined distance and extending beyond the end of the shaft by a distance which determines the depth of incisions made in the corneal tissue of a patient's eye.

BRIEF DESCRIPTION OF THE DRAWINGS

For a more complete understanding of the present invention and the advantages thereof, reference is now made to the following Detailed Description taken in conjunction with the accompanying Drawings in which:

FIG. 3a is a graphic front view of a cornea of a surgically-induced hyperopic eye, illustrating the parallel incisions used in the method of the present invention and the relationship between the dual-cut incisions of the present invention and the single-cut incisions of the previously performed RK surgery;

FIG. 3b is a graphic front view of the cornea of FIG. 3a following the next step of the method of the present invention, illustrating the newly sutured incisions that exert circumferential force on the cornea to increase the corneal curvature;

DETAILED DESCRIPTION OF THE INVENTION

Figure 1:
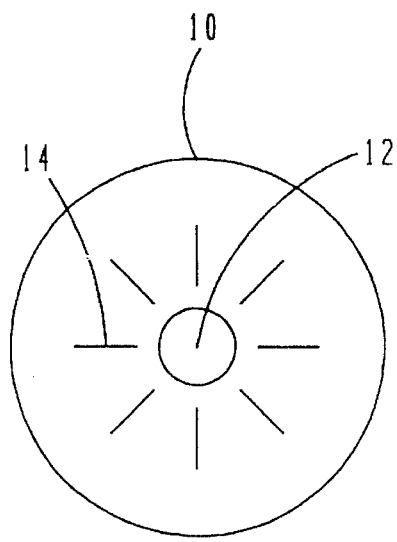
FIG. 1 is a graphic front view of the cornea of a myopic eye following an RK procedure.

Referring now to the Drawings wherein like references characters designate like or similar parts throughout the six views, and in particular to FIG. 1, there is shown a front view of the cornea of a myopic eye following an RK procedure.

The cornea 10 is the clear outer portion of the eye. Light passes through the pupil 12 centrally located behind the cornea 10 to reach the retina (not shown). A series of single-cut, radial incisions 14 have been made in the surface of the cornea 10 during RK to decrease the curvature of the cornea 10 and correct the patient's nearsightedness.

Figure 2:
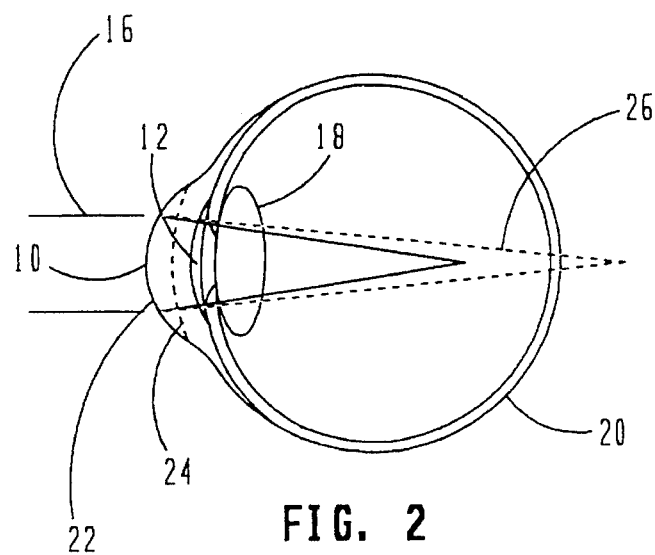
FIG. 2 is a graphic cross-sectional view of the myopic eye of FIG. 1, illustrating the correction to the curvature of the cornea produced by the RK procedure.

FIG. 2 shows a cross-sectional side view of the eye of FIG. 1. Light rays entering the eye create a light path 16 as they pass through the cornea 10, pupil 12 and the lens 18 to form an image on the retina 20, which is then transmitted by the optic nerve (not shown) to the brain. The solid lines in FIG. 2 show the light path prior to the RK procedure. Due to the steep curvature of the natural surface 22 of the cornea 10, the light path 16 focuses at a point in front of the retina 20, rather than directly on it.

Following the RK procedure, the curvature of the cornea 10 has been decreased; the corrected surface 24 of the cornea (shown with dotted lines) is now flatter. The RK procedure was designed to decrease the cornea's curvature so that light rays would focus directly on the retina 20, thereby correcting the myopic eye. As shown in FIG. 2, the RK procedure in this example unintentionally overcorrected the refractive error, that is, the procedure flattened the cornea too much. The corrected light path 26 now focuses on a point behind the retina 20, producing hyperopia. This is the same condition that occurs in a naturally farsighted individual.

Figure 3A:
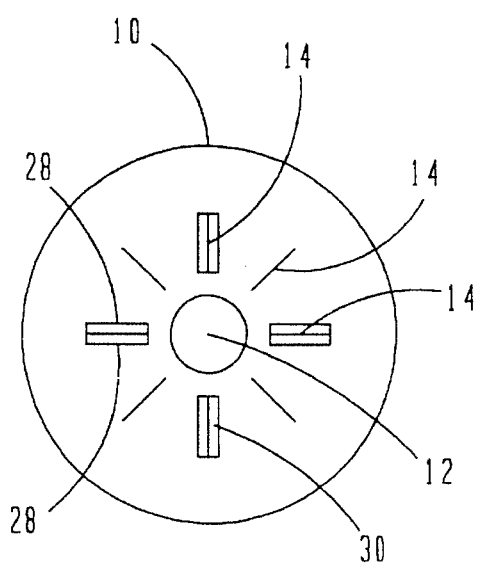
FIGS. 3a and 3b illustrate the method for altering the curvature of the cornea of the present invention.
Figure 3B:
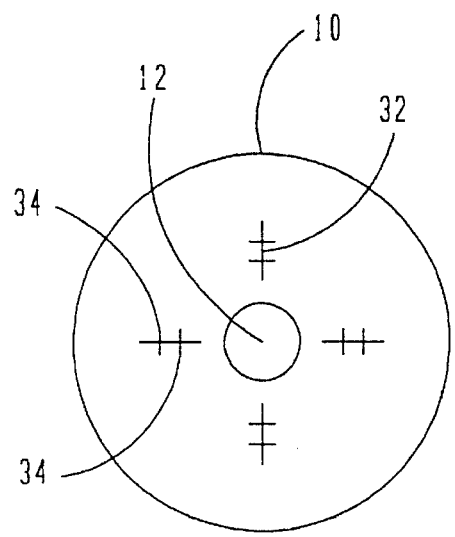

FIGS. 3a and 3b illustrate the method for altering the curvature of the cornea of the present invention. This method may be used to correct naturally occurring and surgically-induced hyperopia. FIG. 3a is a front view of a cornea of a surgically-induced hyperopic eye, such as the one shown in FIGS. 1 and 2. Multiple radial incisions 14 are present from the previously performed RK procedure.

To perform the method of the present invention, the surgeon determines the number, location, length, depth and arrangement of the incisions to be made. The surgeon makes these determinations based on the degree of correction required. For more correction, the surgeon typically will use more incisions.

Through performing many procedures, experienced RK surgeons have learned the degree of correction achieved with the RK procedure. It is known in the art how to adjust the number, location, length, depth and arrangement of incisions to achieve a predictable degree of correction. It is expected that the same empirical methodology will be developed for the present method to be able to adjust various parameters to determine with acceptable precision the degree of correction to change a hyperopic eye to a targeted condition of normal or slightly myopic vision.

In accordance with the preferred method, the surgeon makes multiple pairs 28 of incisions in the surface of the cornea 10. The pairs of incisions 28 are spaced symmetrically and arranged in a radial pattern around the pupil 12.

Each incision in the pair 28 is parallel and closely spaced to the other incision in the pair. The pairs of incisions 28 are not placed in the central cornea; they are located in the periphery of the cornea 10. In the case where the procedure is used to remedy a previous RK procedure which resulted in overcorrection, the pairs of incisions 28 preferably should be placed at the same locations as the prior incisions 14. Based upon the degree of correction required, it may not be necessary to have a pair of incisions 28 adjacent to each of the previous RK incisions. However, it is desirable to have the pairs of incisions 28 located at essentially the same locations as earlier RK incisions 14, each pair of incisions 28 straddling the single incision 14 created during the RK procedure.

The number of pairs of incisions ranges from two to eight, depending on the degree of overcorrection sought to be remedied. At least two pairs of incisions are made in the surface of the cornea 10. A larger amount of overcorrection requires additional pairs of incisions. The pairs of incisions are arranged symmetrically, with their symmetry being a function of the number of cuts. For example, if there are four pairs of incisions, they are typically spaced at 90° intervals.

Each incision in the pairs of incisions may vary in length from 6.0 mm. optical zone to 10.0 mm. optical zone, depending on the amount of correction required. The incisions are made to approximately 90% of the corneal depth.

After a predetermined number of pairs of incisions has been made, the surgeon removes the small portions of corneal tissue 30 located between the pairs of incisions 28. The removed corneal tissue 30 may include some of the RK incisions 14 as well as any scar tissue remaining from the prior RK procedure. Of course, it will be appreciated that although the reversal of an overcorrected RK procedure is an important application of the present invention, it applies as well to the correction of naturally occurring hyperopia.

Turning now to FIG. 3b, there is shown a front view of a cornea following a procedure to reverse overcorrected RK or correct naturally occurring hyperopia. After making multiple pairs of incisions, the corneal tissue in the small space between incisions at each pair site is removed, leaving a narrow gap (not shown). The surgeon draws the walls of cornea at each pair site together forming a single closure 32. The step of closing the gap may be accomplished by stitching, suturing or some other means known in the art. For example, sutures or staples 34 may be used.

By removing small portions of corneal tissue and closing the narrow gap between the incisions, circumferential force is exerted on the surface of the cornea. The curvature of the surface of the cornea is steepened back towards a myopic condition. The cornea is then permitted to heal.

Figure 4:
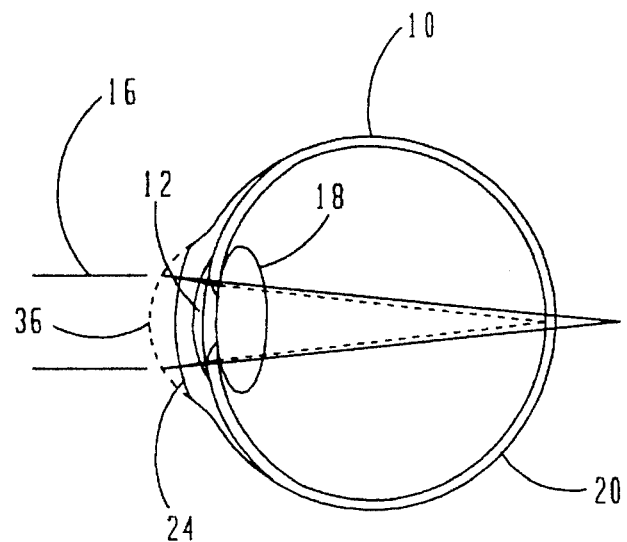
FIG. 4 is a graphic cross-sectional side view of an eye after the method of the present invention has been performed, illustrating the increase in the curvature of the cornea.

Referring now to FIG. 4, therein is shown a cross-sectional side view of an eye after the method of the present invention has been performed. Solid lines illustrate the light path resulting from the overcorrection of the RK procedure. After the RK procedure, light passed through the pupil 12 and the lens 18, creating a light path 16 that focused at a point behind the retina 20. The RK procedure resulted in a flatter corneal surface 24.

Following the method of the present invention, the corneal surface has been increased, thereby changing the focal point of the eye. As shown by the dotted lines, light now focuses on the retina 20, rather than behind it. Internal pressure within the eye created by closing the narrow gap between the incisions at each of several pair sites has forced the cornea to move outwardly. The overcorrected flatter surface 24 of the cornea 10 caused by the previous RK procedure has been reversed to produce a steeper corneal surface 36 and adjust the patient's vision to 20/20 (or very slightly myopic). In this way, a myopic eye which has been altered inadvertently via RK to a hyperopic eye, can be corrected via the method of the present invention to achieve normal eyesight without the need for corrective lenses.

Surgeons typically attempt to correct refractive errors so that the resulting eye will have vision ranging from 20/20 to 20/40. There are instances, however, where the surgeon may wish to correct the eye to a condition outside this range. For example, an objective may be to intentionally create one myopic and one hyperopic eye, producing monovision. Monovision may be desirable for individuals who have normal vision for distances, but who need reading glasses to see near objects. The method of the present invention may be used to surgically change the curvature of one eye so that it is moderately nearsighted. As a result, the individual will be able to read with the slightly myopic eye and see objects at a distance with the other normal or slightly farsighted eye.

The method of the present invention has many applications. It may be used to reverse overcorrection from a previously performed RK, reduce hyperopia in a naturally farsighted eye, or create myopia in a farsighted eye. It may be used to create monovision to compensate for changes that occur as the eyes age. The method may be used to correct many varieties of over- or undercorrection, since the surgeon is able to adjust the amount of correction based on the number, location, length and depth of the incisions, as well as the spacing between the two incisions at each pair site.

The method of the present invention may be performed using the single-blade instruments known in the industry. For example, one such instrument known as a diamond knife is sold under the trademark "DuoTrak" by Magnum Diamond Corp., One Concourse Drive, Rapid City, S. Dak. 57701. The blade can be retracted and the depth of each incision adjusted using a calibration micrometer located remote from the cutting end of the instrument in a similar manner to what is disclosed in U.S. Pat. No. 5,376,099, which is incorporated by reference herein.

Figure 5:
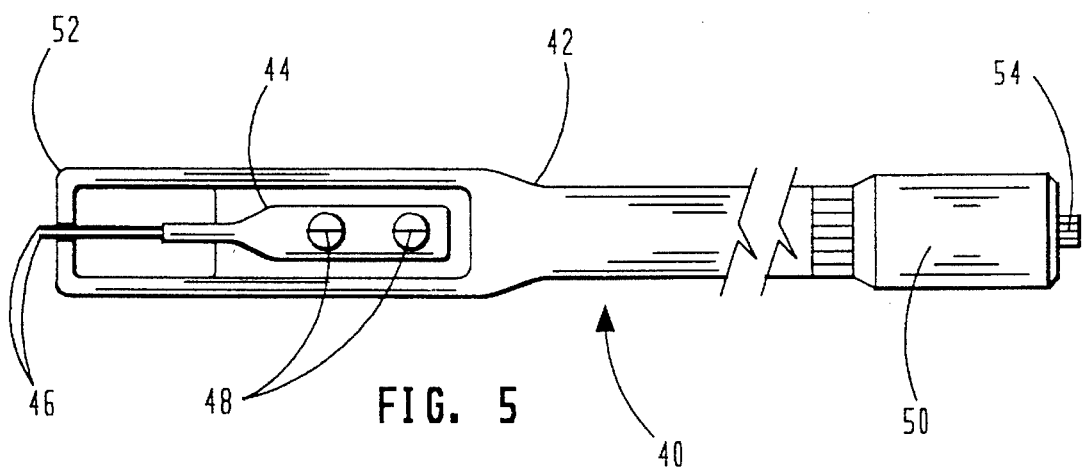
FIG. 5 is a side view of an instrument for altering the curvature of a cornea, illustrating the parallel, double-cutting blades.

In the preferred method, however, it is desirable to use a particular instrument constructed in accordance with another aspect of the present invention. FIG. 5 illustrates a side view of an instrument 40 for altering the curvature of a cornea, illustrating parallel, double-cutting blades. The instrument 40 includes a shaft 42, which is held by the surgeon during the procedure. A replaceable cutting tool 44 is mounted at the cutting end of the shaft 42. The cutting tool 44 is axially positionable with respect to the shaft 42.

A pair of parallel, closely-spaced blades 46 extend from the free end of the cutting tool 44. The blades 46 are separated by a predetermined distance. In the preferred embodiment, the distance between the blades 46 is 0.5 mm. The cutting tool 44 is fastened by suitable means such as screws 48 to an interior portion of the shaft 42. This arrangement facilitates installing tools with various different incremental spacings between the blades 46. By changing the blade spacing, the surgeon can increase or decrease the space between incisions at each pair site on the surface of the cornea to a predetermined separation distance based upon the amount of corneal curvature correction desired.

As an alternative to using replaceable tools with incremental fixed blade spacings, the present invention contemplates the use of a cutting tool having means (not shown) for continuously varying the blade spacing. The surgeon would employ such means with a calibrated microscope to set the blade spacing to a desired distance.

The instrument 40 includes calibration micrometer 50 for adjusting the axial extension of the cutting tool 44 with respect to the shaft 42. In this way, the surgeon can adjust the depth of the incision made by the parallel blades 46 in the surface of the cornea.

Feet 52 are supported at the cutting end of the shaft 42 on either side of and at right angles to the blades 46. The feet 52 rest against the surface of the cornea to determine the depth of the incisions. The blades 46 can be extended by a measured amount beyond the feet 52 using the calibration micrometer 50 in a manner similar to that disclosed in U.S. Pat. No. 5,376,099. Once the desired degree extension of the blades 46 has been selected, the instrument can be locked in that position using a spring-loaded set button 54 at the end of the shaft 42 which prevents inadvertent rotation of the micrometer 50. By depressing the set button to a locked position, internal friction surfaces (not shown) are brought together to hold the micrometer mechanism 50 in a preset position.

To better understand the method of the present invention, the following case studies are included.

Case Study 1:

A 49-year old male underwent an RK procedure in 1982. He obtained a nice result initially, but over the subsequent 12-year interval, his right eye decreased to the 20/100 level. His left eye remained 20/20 since the original surgery. He requested an RK reversal procedure to regain his original post-operative acuity.

In 1994, the patient underwent an RK reversal procedure. Four incisions were removed en block using the above-described method. The four slivers of cornea included the original incisions and were removed on a 6.0 mm. optical zone. The slivers were approximately 0.5 mm. in width and extended from the 6.0 mm. to the 9.0 mm. optical zone. Each of the four areas was reapproximated using two interrupted sutures of 10-0 nylon. The two sutures were placed such that the areas were trisected into three equal segments. The patient was then placed on routine post-operative antibiotic drops.

At three weeks post-operative visit, the patient was significantly nearsighted (−8.00 diopters) and his inner row of sutures was removed. At the ten-week interval, the patient had 20/20 uncorrected visual acuity and the prescription was plano +0.75×65. He was released to future follow-up and on a future visit, his vision remained at the 20/30 to 20/40 level without any visual aids.

Case Study 2:

A 32-year old female underwent an RK procedure originally on both eyes in 1993. Her left eye had an irregular shape and was far more nearsighted than the right eye preoperatively. Her right eye has remained at 20/30 since the original procedure, however, her left eye was initially overcorrected after overresponding to the surgery.

In 1994, the patient underwent a four-incision RK reversal procedure. Four slivers of corneal tissue were removed. Each sliver was approximately 0.8 mm. in width and extended from the 5.0 mm. optical zone to the 9.0 mm. optical zone. Each of the four areas was then reapproximated using two interrupted sutures of 10-0 nylon. They were placed such that the incisional areas were trisected into three equal segments. The patient was then placed on post-operative antibiotics.

At the one-month post-operative visit, the patient had a prescription of −5.00 diopters and was significantly nearsighted. All sutures were removed and she was asked to return in six weeks. When she was last seen at a five months post-operative visit, she had a prescription of −0.50 sphere with uncorrected vision of 20/30.

Case Study 3:

A 47-year old female underwent an uncomplicated RK procedure in November 1993. Both eyes were corrected for distance vision at her request. Both eyes were 20/20 after surgery, however, due to her age, she had significant difficulty with reading. She requested reversal of her non-dominant left eye in order for her to read without glasses.

In 1994, the patient underwent an RK reversal procedure. Three slivers of corneal tissue were removed of 0.5 mm. width each. They extended from the 6.0 mm. optical zone to the 9.0 mm. optical zone. Each of the three areas was closed with two interrupted sutures of 10-0 nylon in order to trisect the incisions into three equal parts. Two of the incisions included the original radial incisions which were removed, and one incision was placed in previously untouched corneal tissue.

At the five-week post-operative visit, the patient was significantly nearsighted and three of the six sutures were removed. At the two-month post-operative visit, the patient was able to read Jaeger 2 print (20/25 at near) and had a prescription of −2.25+1.00 ×15 degrees. At the four-month visit, her prescription was −2.50+0.75×15 degrees and she could read Jaeger 1+print (20/20). She was then released to future follow-up.

Although a preferred embodiment of the present method and instrument has been illustrated in the accompanying Drawings and described in the foregoing Detailed Description of the Invention, it will be appreciated by those skilled in the art that the invention is not limited to the embodiments disclosed, but is capable of numerous rearrangements, modifications, and substitutions of parts and elements without departing from the true spirit of the invention.

I claim:

1. A method for altering the curvature of the cornea of an eye, comprising the steps of:
   (a) making two parallel, closely-spaced incisions in the surface of the cornea at a first site;
   (b) removing the corneal tissue disposed between the two parallel incisions at the first site;
   (c) repeating the above-identified steps at at least a second site on the surface of the cornea; and
   (d) closing the incision at each site.

2. The method of altering the curvature of the cornea of an eye as set forth in claim 1 further comprising the step of predetermining the number, location, length, depth, arrangement and spacing of incisions to be made in the surface of the cornea to achieve a desired correction to the vision of the eye.

3. The method of altering the curvature of the cornea of an eye as set forth in claim 1 wherein the parallel incisions are spaced about 0.5 mm. apart.

4. The method of altering the curvature of the cornea of an eye as set forth in claim 1 wherein the parallel incisions are made in the peripheral surface of the cornea.

5. The method of altering the curvature of the cornea of an eye as set forth in claim 1 wherein the step of closing the incision at each site is accomplished using staples.

6. The method of altering the curvature of the cornea of an eye as set forth in claim 1 wherein the step of closing the incision at each site is accomplished using sutures.

7. The method of altering the curvature of the cornea of an eye as set forth in claim 1 wherein the step of making incisions in the surface of the cornea is performed using an instrument having two parallel blades which are used to cut into the surface of the cornea to a predetermined depth.

8. The method of altering the curvature of the cornea of an eye as set forth in claim 7 further comprising the step prior to the step of making incisions of calibrating the instrument to achieve the predetermined incision depth.

9. The method of claim 1 wherein the parallel incisions at each site are arranged in a radial pattern around the pupil.

10. A method for altering the curvature of the cornea of an eye, comprising the steps of:
    (a) determining the number, location, length, depth, arrangement and spacing of incisions to be made in the surface of the cornea;
    (b) placing an instrument having two parallel blades in contact with the surface of the cornea;
    (c) using the instrument to make parallel incisions in the surface of the cornea at a first predetermined site;
    (d) repeating steps (b) and (c) at at least a second predetermined site on the surface of the cornea;
    (e) removing the corneal tissue disposed between the two parallel incisions forming narrow gaps at the first and subsequent predetermined sites; and
    (f) suturing the resulting gap at each predetermined site to close the wound and apply a circumferential force to the surface of the cornea.

11. The method of altering the curvature of the cornea of an eye as set forth in claim 10 wherein the corneal tissue removed at each site includes preexisting scar tissue from a prior RK procedure to at least partially reverse the optical correction of the prior RK procedure.

12. The method of altering the curvature of the cornea of an eye as set forth in claim 10 wherein the procedure is performed on a naturally hyperopic eye to correct its vision to a normal or slightly myopic condition.

13. The method of claim 10 wherein the parallel incisions at each site are arranged in a radial pattern around the pupil.

14. A method for altering the curvature of the cornea of an eye, comprising the steps of:
    (a) simultaneously forming a first pair of parallel incisions in the cornea of a patient's eye of a predetermined length and depth;
    (b) simultaneously forming a second pair of parallel incisions in the cornea of the patient's eye of a predetermined length and depth;
    (c) removing the corneal tissue between each pair of parallel incisions to leave elongated gap at each pair site oriented radially with respect to the pupil; and
    (d) at each pair site drawing the walls of the cornea together to close the gap, whereby the resulting forces produce a steeper corneal curvature thereby correcting a preexisting hyperopic condition.

15. The method of claim 14 wherein additional pairs of incisions are formed at selected sites in the surface of the cornea in like manner as in steps (a) and (b), and wherein the corneal tissue is removed and the resulting gap closed at each site as in steps (c) and (d).

16. The method of claim 15 wherein the sites for the pairs of parallel incisions are arranged symmetrically, with their symmetry being a function of the number of sites.

17. The method of claim 16 wherein four sites of incision pairs are formed and spaced at 90° intervals around the pupil.

* * * * *